(12) United States Patent
Ekelund et al.

(10) Patent No.: US 9,132,017 B2
(45) Date of Patent: Sep. 15, 2015

(54) ROTATABLE COLLAR FOR A PROSTHESIS

(75) Inventors: Anders Ekelund, Bromma (SE); Sylvain Gauthier, Leeds (GB); Laurent Lafosse, Sevrier (FR); Jack Long, Warsaw, IN (US); Robin Maisonneuve, Chaponnay (FR); Didier Poncet, Leeds (GB)

(73) Assignee: DEPUY (IRELAND) (IE)

( * ) Notice: Subject to any disclaimer, the term of this patent is extended or adjusted under 35 U.S.C. 154(b) by 156 days.

(21) Appl. No.: 13/696,738

(22) PCT Filed: Mar. 29, 2011

(86) PCT No.: PCT/EP2011/054794
§ 371 (c)(1),
(2), (4) Date: Feb. 19, 2013

(87) PCT Pub. No.: WO2011/138090
PCT Pub. Date: Nov. 10, 2011

(65) Prior Publication Data
US 2013/0197652 A1   Aug. 1, 2013

(30) Foreign Application Priority Data

May 7, 2010   (GB) .................................. 1007656.0

(51) Int. Cl.
*A61F 2/32*    (2006.01)
*A61F 2/40*    (2006.01)
(Continued)

(52) U.S. Cl.
CPC ........... *A61F 2/4014* (2013.01); *A61F 2/30728* (2013.01); *A61F 2/4059* (2013.01);
(Continued)

(58) Field of Classification Search
CPC ............ A61F 2/30728; A61F 2/30729; A61F 2/30734; A61F 2/30367; A61F 2/30538; A61F 2/30772; A61F 2002/2825; A61F 2002/2828; A61F 2002/2832; A61F 2002/2853; A61F 2002/30332; A61F 2002/30574; A61F 2002/4033
USPC .......... 623/19.11, 19.12, 19.14, 22.42, 22.43, 623/22.45, 23.21, 23.22, 23.26
See application file for complete search history.

(56) References Cited

U.S. PATENT DOCUMENTS 4,783,192 A  * 11/1988 Wroblewski et al. ...... 623/23.21
5,314,479 A  *  5/1994 Rockwood et al. ........ 623/19.14
(Continued)

FOREIGN PATENT DOCUMENTS

DE          10123517 C1    11/2002
EP           1048274 A2    11/2000
(Continued)

OTHER PUBLICATIONS

PCT International Search Report PCT/EP2011/054794 dated Jun. 8, 2011.
(Continued)

*Primary Examiner* — Randy Shay

(57) ABSTRACT

A collar (2) arranged to couple to a prosthetic component for implantation at the end of a long bone, the prosthetic component having a distal portion arranged to couple to the bone and a proximal neck portion arranged to couple to an articulation component. The collar (2) comprises a plate including a neck hole (4) to receive a neck portion, such that the collar can rotate about the neck portion. The collar (2) further comprises a plurality of attachment portions (12) for coupling the plate to bone fragments or soft tissues. The collar (2) is lockable to the neck portion to prevent further rotation. A prosthesis comprising a combination of a collar (2), a prosthetic component and an articulation component, and a surgical method of using the collar (2) are also disclosed.

13 Claims, 4 Drawing Sheets

(51) Int. Cl.
  *A61F 2/30* (2006.01)
  *A61F 2/46* (2006.01)
  *A61B 17/84* (2006.01)

(52) U.S. Cl.
  CPC .............. *A61F 2/4637* (2013.01); *A61B 17/842* (2013.01); *A61F 2002/30332* (2013.01); *A61F 2002/30367* (2013.01); *A61F 2002/30461* (2013.01); *A61F 2002/30538* (2013.01); *A61F 2002/30729* (2013.01); *A61F 2002/30772* (2013.01); *A61F 2220/0033* (2013.01); *A61F 2220/0075* (2013.01)

(56) References Cited

U.S. PATENT DOCUMENTS

| | | |
|---|---|---|
| 6,398,812 B1 | 6/2002 | Masini |
| 2001/0037152 A1* | 11/2001 | Rockwood, Jr. ........... 623/19.12 |
| 2003/0028253 A1 | 2/2003 | Stone |
| 2004/0225369 A1 | 11/2004 | Lakin |
| 2005/0177241 A1 | 8/2005 | Angibaud |
| 2006/0009852 A1 | 1/2006 | Winslow |
| 2007/0118230 A1 | 5/2007 | Callaway |
| 2007/0173945 A1 | 7/2007 | Wiley |

FOREIGN PATENT DOCUMENTS

| | | |
|---|---|---|
| EP | 2133041 A1 | 12/2009 |
| FR | 2939639 A1 | 6/2010 |
| WO | WO 9309733 A1 | 5/1993 |
| WO | WO 2011023921 A1 * | 3/2011 |

OTHER PUBLICATIONS

UK Search Report GB1007656.0 dated Sep. 2, 2010.
JP Office Action JP Application No. 2013-508414 dated Jan. 27, 2015.

* cited by examiner

ROTATABLE COLLAR FOR A PROSTHESIS

CROSS REFERENCE TO RELATED APPLICATION

This application is a National Stage 35U.S.C. 371of International Patent Application PCT/EP2011/054794filed Mar. 29, 2011.

BACKGROUND OF THE INVENTION

The present invention relates generally to orthopaedic surgery and in particular to shoulder prostheses. More particularly, the present invention relates to a rotatable collar forming part of a humeral prosthesis. Alternatively, the rotatable collar may form part of a femoral prosthesis. The present invention also relates to an assembled prosthesis and a surgical shoulder arthroplasty procedure using the humeral prosthesis.

A natural shoulder joint may undergo degenerative changes for a variety of reasons, for instance arthritis. Alternatively, a shoulder joint may be fractured or otherwise damaged by an external force. When a shoulder joint is sufficiently degenerated or damaged it may be necessary to replace a natural shoulder with a prosthetic shoulder joint. Conventional shoulder prostheses comprise a humeral prosthesis, optionally with a glenoid prosthesis. For total or reverse arthroplasty a glenoid component is implanted, however for hemi arthroplasty the humeral component articulates against the natural glenoid cavity.

Typically, the humeral component comprises a stem for insertion into a bore extending into the intramedullary canal generally along the longitudinal axis of the bone and an articulation component, which may be a convex bearing head in the case of total arthroplasty or a concave cup in the case of reverse arthroplasty. Typically, the articulation component is coupled to a neck portion of the stem, which extends from the intramedullary canal at an inclined angle relative to the longitudinal axis of a distal portion of the stem in order to recreate the arrangement of the natural joint.

When the upper extremity of the humerus is fractured, the humerus generally breaks into several pieces, typically three or four. In particular, for "four part fractures" the humeral head splits off at the level of the anatomical neck, the greater and lesser tuberosities are separated from the humerus shaft below the tuberosities and the tuberosities are separated from one another along the bicipetal groove. As there is no longer a blood supply to the humeral head necrosis may begin. For repair of a four part fracture, the humeral head is replaced, and the greater and lesser tuberosities are reattached to the humeral shaft. Known shoulder prostheses for repair of a four part fracture provide tabs or fins attached to the stem which incorporate holes to receive sutures to couple the tuberosities and soft tissue such as tendons to the prosthesis. Correct positioning of the suture holes is essential to accommodate the differing attachment point of soft tissues to the humerus in a natural joint. For instance, U.S. Pat. No. 6,398,812 discloses a shoulder prosthesis with anatomic reattachment features for tendon or bone in which at least one set of tendon or bone reattachment features are provided along a line which is divergent with respect to the axis of the stem. This provides for reattachment of tendons, such as the supraspinatus tendon, which naturally lie along the top surface of the humerus.

US-2005/0177241 discloses an alternative humeral prosthesis in which a stem is anchored in the intramedullary canal and a metaphyseal portion extends upwardly from the stem and is joined to a flange supporting a prosthetic head. The primary purpose of the flange is to transfer force to the humeral shaft. The flange includes suture holes, for instance on its upper extremity, for suturing the tuberosities and soft tissue to the humeral prosthesis.

US-2007/0173945 discloses an implant system for total or hemi shoulder arthroplasties comprising a humeral stem having an enlarged head portion to receive modular interchangeable components, such as articulating liners, spacers and adapter inserts. The head comprises an annular outer rim incorporating a plurality of suture holes for reconstructing the proximal humerus for the repair of humeral fractures.

While it is known, for instance in the above discussed patent publications, to provide suitable attachment points for coupling bone fragments and soft tissue to a prosthesis implanted into the end of a long bone, known prostheses suffer from inflexibility in the position of attachment points which may result in loss of mobility for the repaired joint. It is an object of embodiments of the present invention to obviate or mitigate one or more of the problems of the prior art, whether identified herein or elsewhere.

BRIEF SUMMARY OF THE INVENTION.

According to a first aspect of the present invention there is provided collar arranged to couple to a prosthetic component for implantation at the end of a long bone, the prosthetic component having a distal portion arranged to couple to the bone and a proximal neck portion arranged to couple to an articulation component, wherein the collar comprises a plate including a neck hole to receive a neck portion, such that the collar can rotate about the neck portion, and a plurality of attachment portions for coupling the plate to bone fragments or soft tissues, and wherein the collar is lockable to the neck portion to prevent further rotation.

An advantage of the present invention is that as the collar can rotate around the neck of the stem the attachment points can be provided at the appropriate position about the stem for coupling detached bone fragments and soft tissue. Furthermore, the rotatable collar enables an enhanced surgical technique in which the bone and tissue is attached to the collar and then the collar is rotated to assess and balance loading in the cuff muscles and other soft tissue. When the prosthesis is fully assembled the collar is positioned under the articulation component.

The present invention is particularly suitable for forming part of a humeral prosthesis to repair a four part humeral fracture. Advantageously, the collar may be larger than for fixed flanges incorporating suture holes in known humeral prostheses as for a fixed flange in order to prevent the flange extending beyond the edge of an articulation component the flange must be smaller than the smallest articulation which could be coupled to the neck portion. Furthermore, the bone fragments and soft tissue may be coupled to the humeral prosthesis before final selection of the articulation component which provides greater access to the suture attachment points than for monobloc humeral prostheses.

The neck hole may comprise a tapered bore arranged to form a taper lock to a tapered neck portion when the collar is subjected to an impaction force. The collar may further comprise a raised rim surrounding the neck hole extending the tapered bore such that the tapered bore is deeper than the depth of the remainder of the plate.

The plate may have a periphery formed from a first curved edge defined by a first radius and a second curved edge defined by a second radius which is larger than the first radius. The origin of the first radius may lie within the neck hole. The plurality of attachment portions may be distributed about the periphery of the plate along the first curved section At least one of the plurality of attachment portions may comprise a suture hole arranged to receive and secure a first end of a suture. Additionally, or alternatively, at least one of the plurality of attachment portions may comprise an attached suture extending from the collar. The at least one attached suture may terminate in a needle or a bone anchor.

The collar may further comprise at least one locking hole arranged to couple to an impactor for transferring an impaction force from the impactor to the collar.

According to a second aspect of the present invention there is provided a prosthesis comprising: a collar as described above; a prosthetic component having a distal portion arranged to be coupled to an end of a bone and a proximal neck portion; and an articulation component arranged to couple to the neck portion.

The neck portion may extend along an axis which is inclined to a longitudinal axis of the distal portion, and wherein the collar when coupled to the neck portion lies in a plane which is perpendicular to the neck axis. When the prosthesis is assembled and implanted the attachment portions may be positioned laterally, anteriorly and posteriorly about the end of the bone.

According to a third aspect of the present invention there is provided an implant assembly comprising; a prosthesis as described above, wherein the collar comprises at least one locking hole; and an impactor comprising a handle coupled to a shell arranged to fit over the neck portion, the shell having at least one pin arranged to engage the locking hole such that rotating the handle causes the collar to rotate about the neck portion and applying an impaction force to the handle transfers an impaction force to the collar locking the collar to the neck portion.

According to a fourth aspect of the present invention there is provided a surgical method comprising: resecting a proximal end of a bone; coupling a distal portion of a prosthetic component to the resected end of the bone, the prosthesis further comprising a proximal neck portion extending from the end of the bone; positioning a collar over the neck portion, wherein the collar comprises a plate including a neck hole to receive the neck portion and a plurality of attachment portions; rotating the collar about the neck portion; applying an impaction force to the collar to lock the collar to the neck portion to prevent further rotation; coupling the attachment portion to bone fragments or soft tissues; and coupling an articulation component to the neck portion.

According to a fifth aspect of the present invention there is provided a surgical method comprising: resecting a proximal end of a bone; coupling a distal portion of a prosthetic component to the resected end of the bone, the prosthesis further comprising a proximal neck portion extending from the end of the bone; positioning a collar over the neck portion, wherein the collar comprises a plate including a neck hole to receive the neck portion and a plurality of attachment portions; coupling the attachment portion to bone fragments or soft tissues; rotating the collar about the neck portion to adjust the tension in the soft tissues; applying an impaction force to the collar to lock the collar to the neck portion to prevent further rotation; and coupling an articulation component to the neck portion.

BRIEF DESCRIPTION OF THE DRAWINGS

The present invention will now be described, by way of example only, with reference to the accompanying drawings, in which.

DETAILED DESCRIPTION OF THE INVENTION

Figure 1:
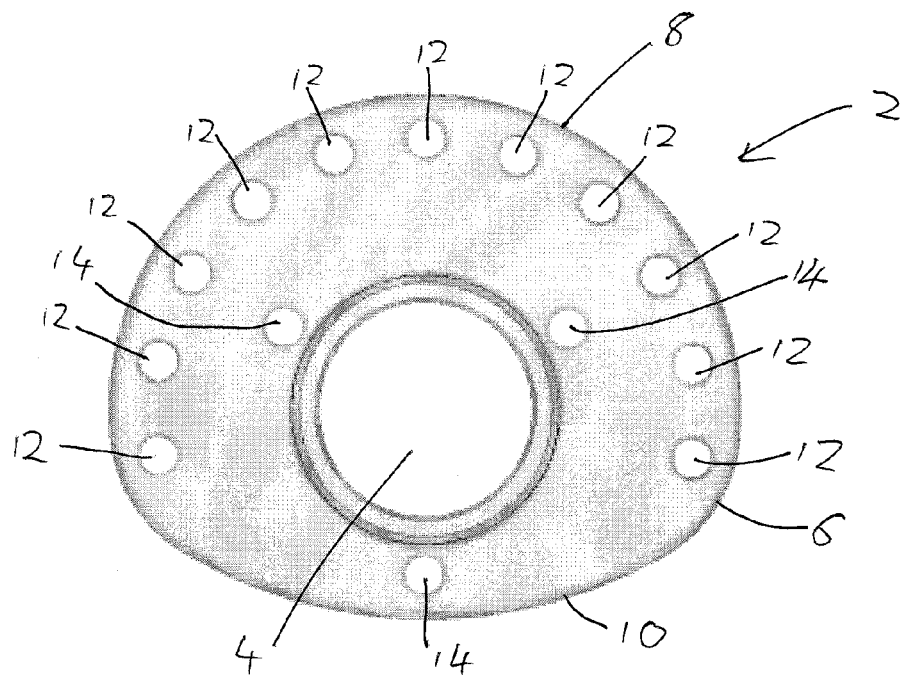
FIG. 1 is a superior view of a collar in accordance with a first embodiment of the present invention.

Referring first to FIG. 1, this is a superior view of a rotatable collar 2 in accordance with a first embodiment of the present invention. The collar 2 comprises a generally planar plate of a metal of generally uniform thickness, for instance approximately 2 mm. The collar 2 incorporates a neck hole 4 arranged to receive a neck portion of a humeral stem, as will be explained below in connection with FIGS. 2 and 3. The collar 2 is arranged to be positioned underneath an articulation component coupled to the neck portion of the stem, together forming a humeral prosthesis. The collar 2 is sized such that when the humeral prosthesis is assembled the collar 2 does not extend beyond the articulation component. This prevents the collar from limiting the range of motion of the assembled joint and to avoid conflict with glenoid bone.

Collar 2 has a periphery 6 formed from a first curved portion 8 defined by a first radius and a second curved portion 10 defined by a second radius, the second radius being larger than the first radius. The neck hole 4 is generally positioned about the origin of the first radius, though not necessarily aligned with the origin. The first radius of the collar defining the first curved portion may be the same as, or smaller than, the radius of the articulation component such that if the articulation component is centred about the axis of the neck hole portion the collar cannot extend beyond the periphery of the articulation component. This prevents the collar from coming into contact with the glenoid bone. As the collar is a separate component to the neck portion this allows the collar to be provided in a range of sizes to allow the largest collar possible to be selected that does not extend beyond the articulation component. Having a larger collar can make it easier to couple bone fragments and soft tissue to the prosthesis. If an eccentric articulation component is used then the size of the collar is restricted such that the maximum radius of the collar from the centre of the neck hole does not exceed the minimum radius of the eccentric articulation component.

Alternatively, if an eccentric articulation component is to be used then a similarly eccentric collar may be provided (that is, the centre of the neck hole is not aligned with the origin of the first radius). The second curved portion 10 lies within a circle defined by the first radius from its origin. The transitions between the first and second curved portions 8, 10 are smoothed.

The first radius may vary between 15 mm and 30 mm, for instance between 19 mm and 25.5 mm according to the size of collar required for a particular patient, and in particular according to the size of the articulation component.

The collar 2 has an array of suture holes 12 which are arranged to lie generally positioned laterally, anteriorly and posteriorly when the humeral prosthesis is assembled and implanted. Specifically, the suture holes 12 are provided proximal to the periphery 6 through the first curved portion 8. Sutures may be passed through any or all of the suture holes 12 in order to secure bone fragments and soft tissues such as tendons to the humeral prosthesis. The number and position of the suture holes may vary. For instance, there may be eleven suture holes evenly spaced apart and centred about the middle portion of the first curved portion 8. Each suture hole may be separated from the neighbouring holes by an angle of 20° measured from the origin of the first radius. The suture holes may be approximately 2.5 mm in diameter.

The collar 2 further comprises three holes 14 positioned about the neck hole 4. Holes 14 are shown evenly distributed and spaced about the neck hole 4 spaced apart by 120° from one another about the origin of the first radius defining the first curved portion 8, but this need not be the case. Holes 14 are arranged to engage a collar impactor tool, as will be described below in connection with FIG. 4. It will be appreciated that holes 14 are only one exemplary form of locking system for locking to a collar impactor tool. Further locking mechanism, such as those used for other forms of surgical impactor tools, will be readily apparent to the appropriately skilled person.

Figure 2:
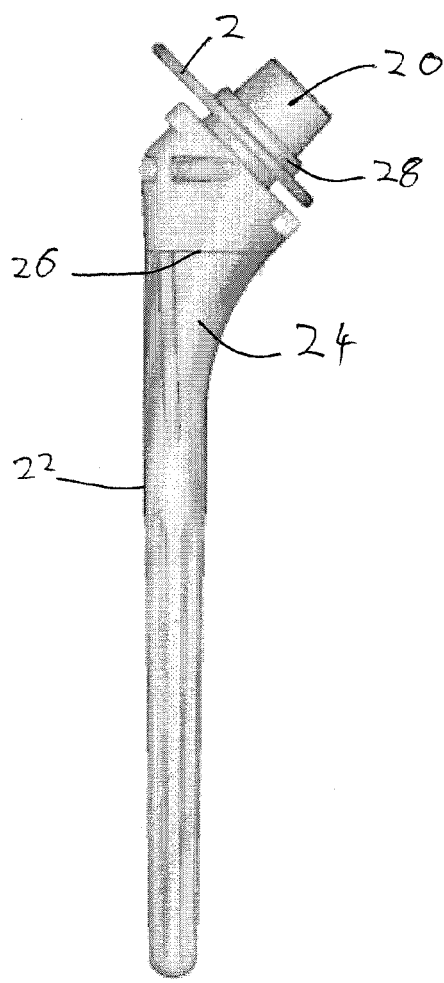
FIG. 2 is an anterior view of the collar of FIG. 1 removably attached to a stem of a humeral prosthesis.
Figure 3:
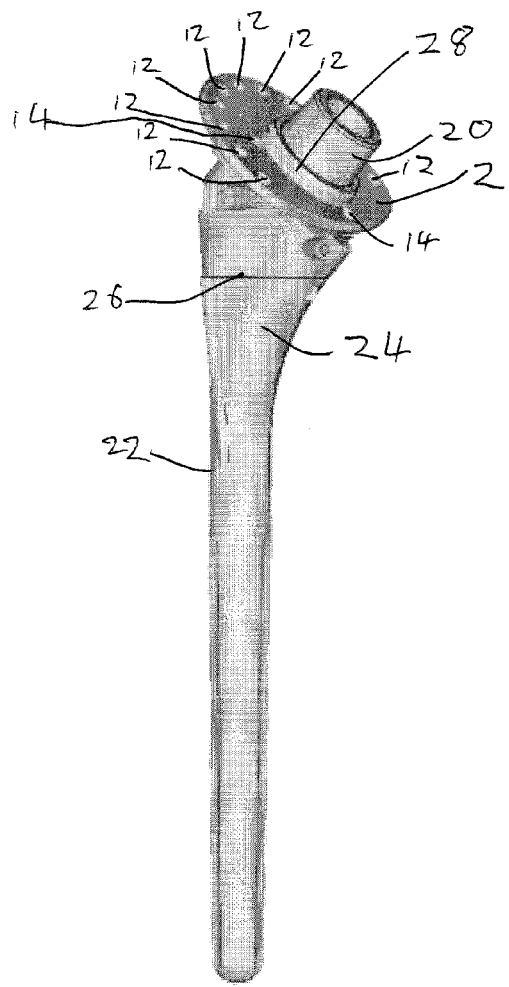
FIG. 3 is a perspective view of the collar and stem of FIG. 2.

Referring now to FIGS. 2 and 3, these illustrate an anterior view and a perspective view respectively of the collar 2 coupled to a neck portion 20 of a stem 22. The neck portion 20 extends from the remainder of the stem 22 at an inclined angle to the longitudinal axis 24 of a distal part of the stem 22. The stem 20 may be formed from a single piece of metal, or the neck portion 20 may be formed separately and joined to the remainder of the stem 22 below the collar along line 26 as shown. The stem 22 may be generally conventional and so is not described in further detail except in so far as the shape of the stem 22 affects the coupling of the collar 2 to the stem 22. The stem 22 may be suitable for use either within a fracture repair humeral prosthesis of the type discussed herein or within a prosthesis for the repair of a joint where the articulation surfaces are damaged.

The neck portion 20 is frustoconical, and tapers away from the stem 22. The distal end of the neck portion 20 is hollow for coupling to the articulation component. Surrounding the neck hole 4 is a raised rim 28 extending proximally from the proximal surface of the collar 2. The rim may extend the thickness of the plate to approximately 4.5 mm Rim 28 and neck hole 4 in combination define a tapered bore corresponding to the taper of the neck portion 20. The edges of the bore may taper towards one another at an angle of between 5° and 6°, for instance 5.653°. The maximum diameter of the bore is dependent upon the size of the prosthesis neck portion. It may typically be approximately 14.7 mm. An axis defined by the tapered bore is perpendicular to the plane of the outer portions of the plate. When the collar 2 is positioned over the neck portion 20 it is initially free to rotate about the neck portion 20. However, subjecting the collar 2 to an impaction force along the axis of the neck portion compresses the collar 2 over the neck portion 20 forming a taper lock.

Figure 4:
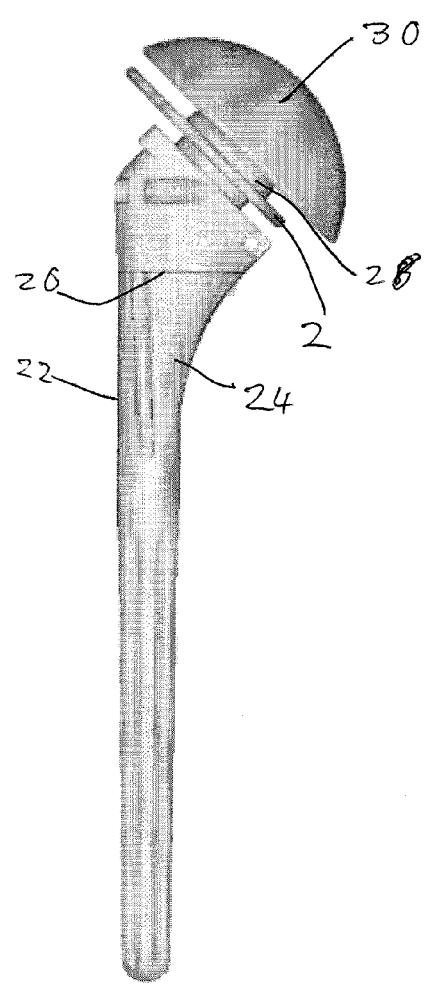
FIG. 4 is an anterior view of the collar of FIG. 1 removably attached to a stem of a humeral prosthesis and an articulation component attached to the proximal end of the stem.

FIG. 4 is an anterior view of the collar 2 coupled to a neck portion 20 of a stem 22, generally the same as for that of FIG. 2, except that coupled to the proximal end of the neck portion 20 is an articulation component 30. Articulation component 30 is illustrated as a convex bearing head forming part of a prosthesis for total or hemi shoulder arthroplasty. For a reverse shoulder arthroplasty the convex bearing head would be replaced by a concave cup. It can be seen that the articulation component is spaced apart from the collar 2. The collar 2 does not extend beyond the articulation component 30 in any direction perpendicular to the axis of the neck portion 20.

Figure 5:
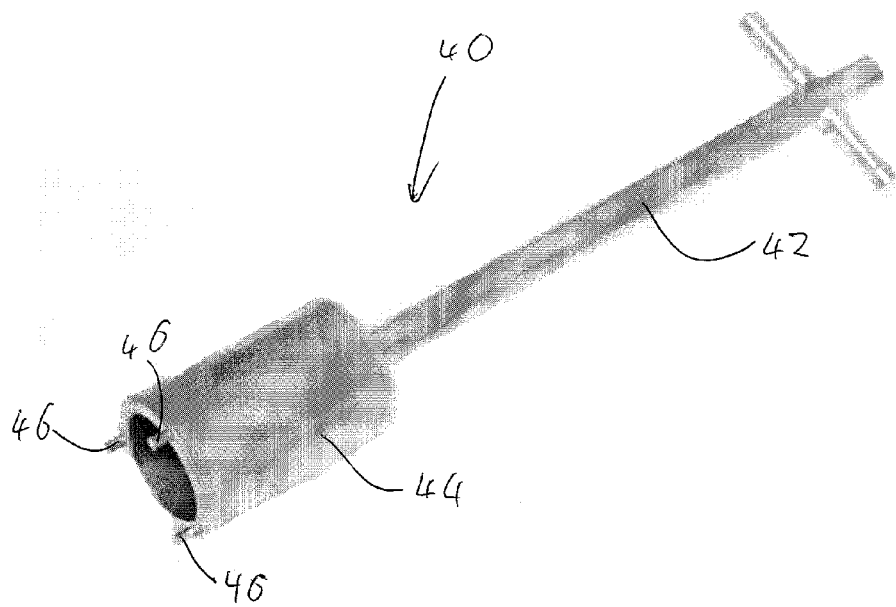
FIG. 5 is a collar impactor for attaching the collar of FIG. 1 to a stem of a humeral prosthesis.

Referring now to FIG. 5, this illustrates a collar impactor 40 for securing the taper lock between the collar 2 and the neck portion 20 preventing further rotation of the collar 2. The impactor 40 comprises a handle 42 terminating in a shell 44 arranged to pass over rim 28 of the collar 2 and neck portion 20 of the stem 22. The open end of the shell 44 comprises pins 46 arranged to be received in the holes 14 around the neck hole 4 in the collar 2. Engaging the holes 14 with the pins 46 allows the collar 2 to be rotated to the required position about the neck portion 20 of the stem implant. Once the correct rotational position is achieved an impaction force may be applied to the handle 42 to secure the taper lock.

Figure 6:
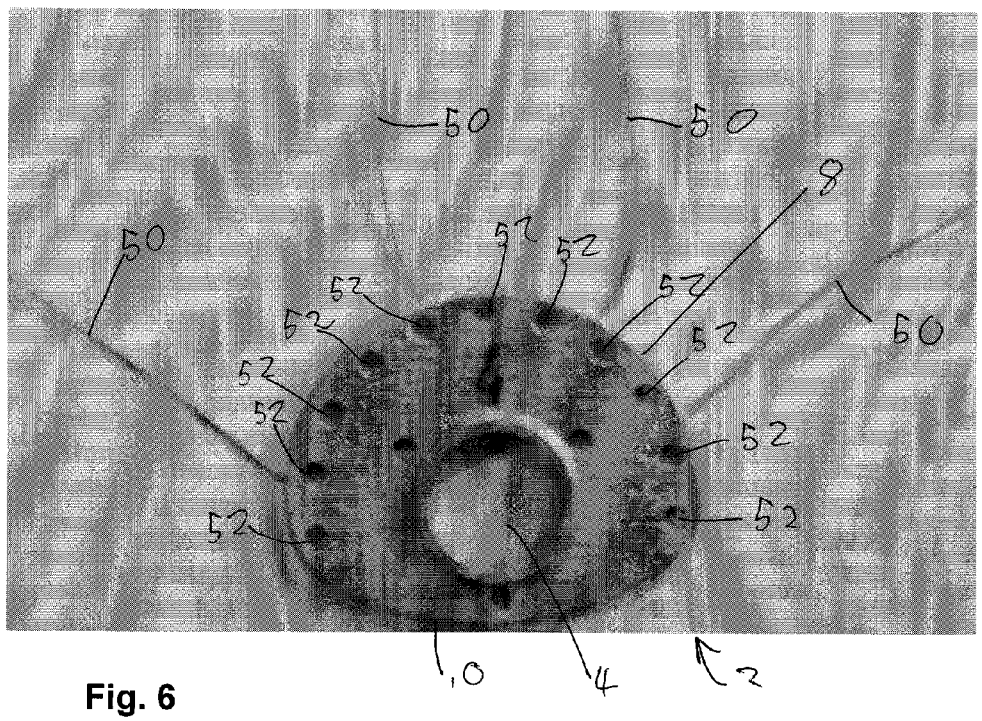
FIG. 6 is a superior view of a collar in accordance with a second embodiment of the present invention.

Referring now to FIG. 6, this illustrates a collar 2 in accordance with a second embodiment of the present invention. Where features of the collar of FIG. 6 are the same as for the collar 2 of FIG. 1 the same reference numbers are used. In place, or in addition to, the suture holes 12 of FIG. 1, the collar 2 of FIG. 6 has sutures 50 permanently coupled to or preattached to the plate around the periphery. The sutures may extend from the edge of the plate or from an upper or lower surface of the plate. The sutures may be attached for instance by crimping or by being tied to a suture hole.

Some or all of the sutures 50 may terminate at needles and/or anchors for coupling to bone or soft tissue, or alternatively conventional surgical techniques may be used to attach the sutures to bone or soft tissue. The needles or anchors may be entirely conventional and so are not further described. The collar 2 may also or alternatively comprise multifunctional holes 52 about the periphery of the plate. Preferably the multifunctional holes are positioned along the first curved portion 8 proximal to the fixed sutures. The multifunctional holes 52 may be arranged to receive temporary guide pins or wires during the implantation process that are removed before the surgical procedure is complete. The multifunctional holes may be generally the same as the suture holes within the collar illustrated in FIG. 1. The multifunctional holes may also be used to couple bone or tissue to the collar with sutures.

Figure 7:
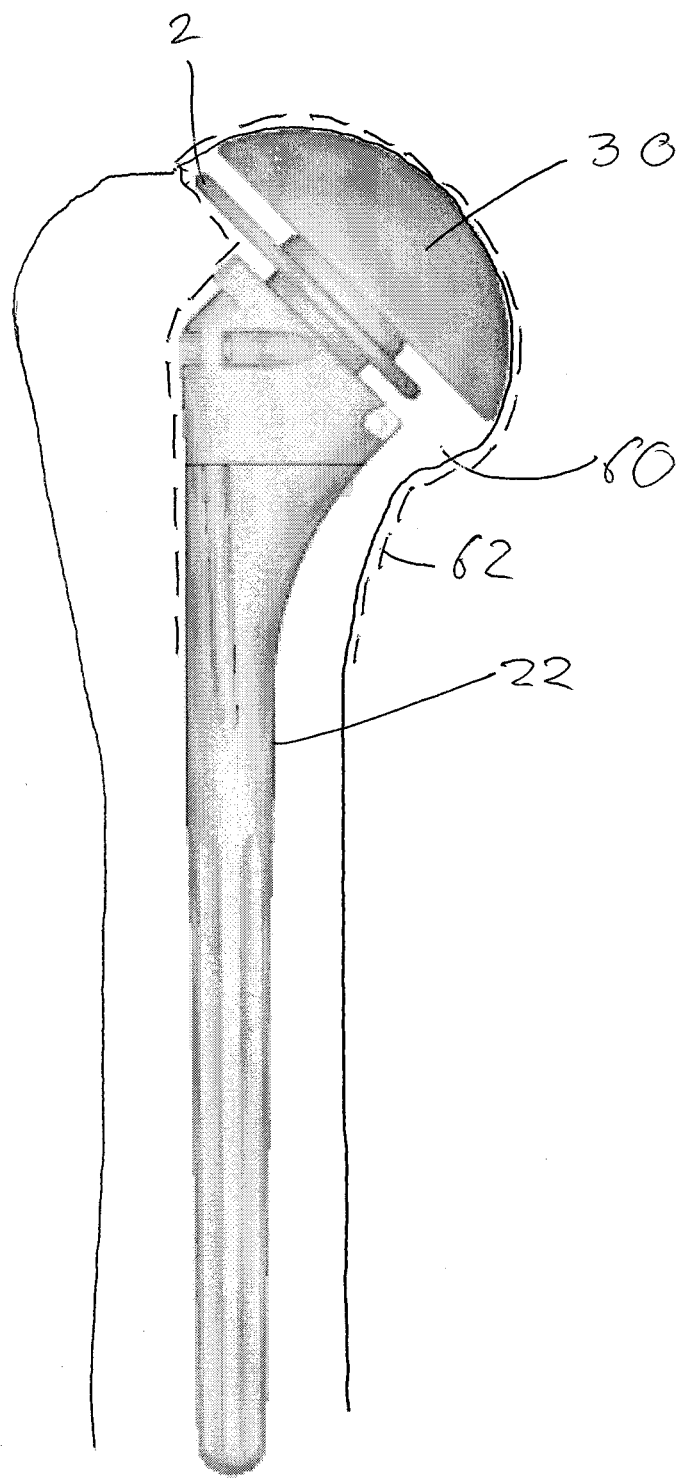
FIG. 7 is a partial cross sectional view in a frontal plane of the collar of FIG. 1 removably attached to a stem of a humeral prosthesis and an articulation component attached to the proximal end of the stem, the prosthesis being coupled to a bone.

Referring now to FIG. 7, this illustrates a collar 2 coupled to a neck portion of a stem 22, in the same view as FIG. 4 in a frontal plane coupled to a humeral head 60. In particular, portions of the bone overlying the prosthesis are omitted to allow the whole prosthesis to be seen. Furthermore, those portions of the head of the humerus that are removed during the implantation of the prosthesis (the articulation surface and bone within a bore extending along the medullary canal) are shown by dashed lines 62.

A surgical procedure for implanting the prosthesis illustrated in FIG. 7 to repair a fractured humeral head will now be described. It will be appreciated that details of the surgical procedure may vary, for instance according to the preferences of the surgeon. As discussed above, the collar of the present invention may be indicated for repair of three-part or four-part proximal humeral fractures. In a four-part proximal humeral fracture the humeral head is a free fragment not coupled to any soft tissue and deprived of a blood supply. The greater and lesser tuberosities are detached. The greater tuberosity is displaced superiorly and posteriorly by the attached rotator cuff, while the lesser tuberosity is retracted medially by the attached subscapularis. The fractured end of the humeral shaft is displaced medially by the pull of the pectoralis major. Three-part fractures differ in that the lesser tuberosity remains attached to the humeral head, which in consequence is rotated internally by the subscapularis tendon.

The surgeon must first gain access to the fractured humeral head. The patient must be positioned so as to allow the surgeon free access to the injured shoulder, for instance in a "beach chair" position, with the injured arm hanging free, providing spaced for later manipulation of the arm. The fracture may be examined using fluoroscopy, including under internal and external rotation. A deltopectoral exposure may be used to identify the coracoid, acromium and deltoid insertion. The interval between the pectoralis and the deltoid is developed and the incision line is extended distally from the coracoids.

The exposure is through a 12-14 cm incision. The incision may be held open using self retaining retractors. Care must be taken to identify and retract the cephalic vein. The coracobrachialis is retracted medially and the pectoralis insertion at the floor of the deltopectoral interval is located allowing the subacromial space to be developed to mobilise the proximal deltoid.

The detached humeral head may then be removed (after releasing the head from the lesser tuberosity in the case of a three-part fracture). The appropriate size of articulation component 30 may then be chosen, for instance by comparing the humeral head to a gauge to measure its height and radius of curvature. The tuberosities must also be released from underlying soft tissues, taking care to protect the axillary nerve when mobilising the lesser tuberosity and the attached subscapularis muscle tendon. The tuberosities are released so as to allow them to be coupled to each other and to the arthroplasty plate, passing around the prosthesis.

A bore is then formed extending into the medullary canal of the humerus. The proximal part of the bore may be further enlarged to receive the neck portion of the humeral stem, which is inserted into the bore so that the neck portion protrudes from the bore.

In a first option, the collar may be positioned on the neck portion at the required rotational position and locked to the neck portion using the impactor. Bone fragments and soft tissue may then be coupled to the collar using sutures as described above before the articulation component is attached to the neck portion. Depending upon the nature of the humeral fracture, it may not be necessary to use all of the suture holes. The collar is rotated until the suture holes are presented in the optimum rotational position for securing bone fragments and soft tissues.

Alternatively, before the collar is locked in position the bone fragments and soft tissue may be coupled to the collar. Rotation of the collar allows the correct tension in the cuff muscles and other tissues to be assessed, balanced and set. The collar may then be locked to the neck portion and the articulation component attached. According to the required form of shoulder prosthesis, the articulation component may be either a convex bearing head or a concave cup. Preferably the articulation component is larger than the collar such that the collar does not protrude from the sides of the articulation component. An axis of the articulation component may be aligned with the neck axis.

The collar may be provided in a range of sizes corresponding to a range of sizes and shapes of articulation components. Additionally, a range of sizes of neck holes within the collars may be provided for locking to humeral stems having neck portions of different diameters.

The collar of the present invention has been primarily described above as forming part of a humeral prosthesis. The collar is particularly suitable for the repair of shoulder fracture indications because there are typically four portions of fractured bone, and so the collar assists in retaining the bone fragments. However, the collar may also form part of a modular prosthesis for implantation into another end of a long bone. For instance, the collar may form part of a femoral prosthesis for the repair of hip fractures. Commonly, the femur fractures across the neck. However, for some forms of femoral fracture, there are multiple portions of fractured bone and so the collar of the present invention may be useful for fixing the bone fragments in position.

More generally, the collar of the present invention has been described above as forming part of a prosthesis for implantation at an end of a long bone, wherein the prosthesis further comprises a distal stem for insertion into an intramedullary bore, a proximal neck portion extending from the end of the bone. However, the collar is not limited to such a form of prosthesis. Rather, the collar may be applied to any prosthesis which includes a proximal neck portion extending from the end of the bone arranged to receive a modular articulation component. For instance, in place of a long stemmed prosthesis, a short stem may be provided implanted within a humeral or femoral neck. Alternatively, the neck portion may be coupled directly to a bone plate attached to the bone.

Other modifications to, and applications of, the present invention will be readily apparent from the teaching herein without departing from the scope of the appended claims.

The invention claimed is:

1. A prosthesis, comprising:
  a prosthetic component having a distal portion arranged to be coupled to an end of a bone and a proximal neck portion, the distal portion having a longitudinal axis;
  an articulation component arranged to couple to the neck portion; and
  a collar comprising a plate having a neck hole, the neck hole and neck portion being sized and adapted such that the neck portion is received within the neck hole, the collar being rotatable about the neck portion when the neck hole receives the neck portion, the collar having a plurality of holes for coupling the plate to bone fragments or soft tissue, and wherein the collar is lockable with respect to the neck portion to prevent rotation; wherein the neck hole is defined by a tapered bore and wherein the plate has a thickness and includes a raised rim extending about the neck hole, the rim being shaped to extend the tapered bore such that the tapered bore is deeper than the thickness of the plate.

2. The prosthesis of claim 1, wherein the neck portion extends along a neck axis that is inclined to the longitudinal axis, and wherein the collar when coupled to the neck portion lies in a plane that is substantially perpendicular to the neck axis.

3. The prosthesis of claim 1, wherein when the prosthesis is assembled and implanted the plurality of holes are positioned laterally, anteriorly and posteriorly about the end of the bone.

4. The prosthesis of claim 1, wherein the plate has a periphery formed from a first curved edge, defined by a first radius, and a second curved edge, defined by a second radius, the second radius being larger than the first radius.

5. The prosthesis of claim 4, wherein an origin of the first radius lies within the neck hole.

6. The prosthesis of claim 4, wherein the plurality of holes are distributed about the periphery of the plate along a first curved section.

7. The prosthesis of claim 1, wherein at least one of the plurality of holes comprises a suture secured thereto.

8. The prosthesis of claim 1, wherein at least one of the plurality of holes comprises at least one attached suture extending from the collar.

9. The prosthesis of claim 8, wherein at least one attached suture terminates in a needle or a bone anchor.

10. The prosthesis of claim 1, wherein the plate has at least one locking hole arranged to couple to an impactor for transferring an impaction force from the impactor to the collar.

11. An implant system, comprising:
the prosthesis of claim 1, wherein the collar has at least one locking hole; and
an impactor comprising a handle coupled to a shell arranged to fit over the neck portion, the shell having at least one pin arranged to engage the locking hole such that rotating the handle causes the collar to rotate about the neck portion and applying an impaction force to the handle transfers an impaction force to the collar locking the collar to the neck portion.

12. A surgical method comprising the steps of:
resecting a proximal end of a bone;
coupling a distal portion of a prosthetic component to the resected end of the bone, the prosthesis further comprising a proximal neck portion extending from the end of the bone;
positioning a collar over the neck portion, wherein the collar comprises a plate including a neck hole to receive the neck portion and a plurality of attachment holes, wherein the neck hole is defined by a tapered bore and wherein the plate has a thickness and includes a raised rim extending about the neck hole, the rim being shaped to extend the tapered bore such that the tapered bore is deeper than the thickness of the plate;
rotating the collar about the neck portion;
applying an impaction force to the collar to lock the collar to the neck portion to prevent further rotation;
coupling at least one of the plurality of holes to bone fragments or soft tissue; and
coupling an articulation component to the neck portion.

13. A surgical method comprising:
resecting a proximal end of a bone;
coupling a distal portion of a prosthetic component to the resected end of the bone, the prosthesis further comprising a proximal neck portion extending from the end of the bone;
positioning a collar about the neck portion, wherein the collar comprises a plate including a neck hole to receive the neck portion and a plurality of attachment holes, wherein the neck hole is defined by a tapered bore and wherein the plate has a thickness and includes a raised rim extending about the neck hole, the rim being shaped to extend the tapered bore such that the tapered bore is deeper than the thickness of the plate;
coupling at least one of the attachment holes to bone fragments or soft tissues;
rotating the collar about the neck portion to adjust the tension in the bone fragments or soft tissues;
applying an impaction force to the collar to lock the collar to the neck portion to prevent further rotation; and
coupling an articulation component to the neck portion.

* * * * *